March 16, 1948. H. C. SWIM Plant Pat. 791
ROSE PLANT
Filed Feb. 13, 1947
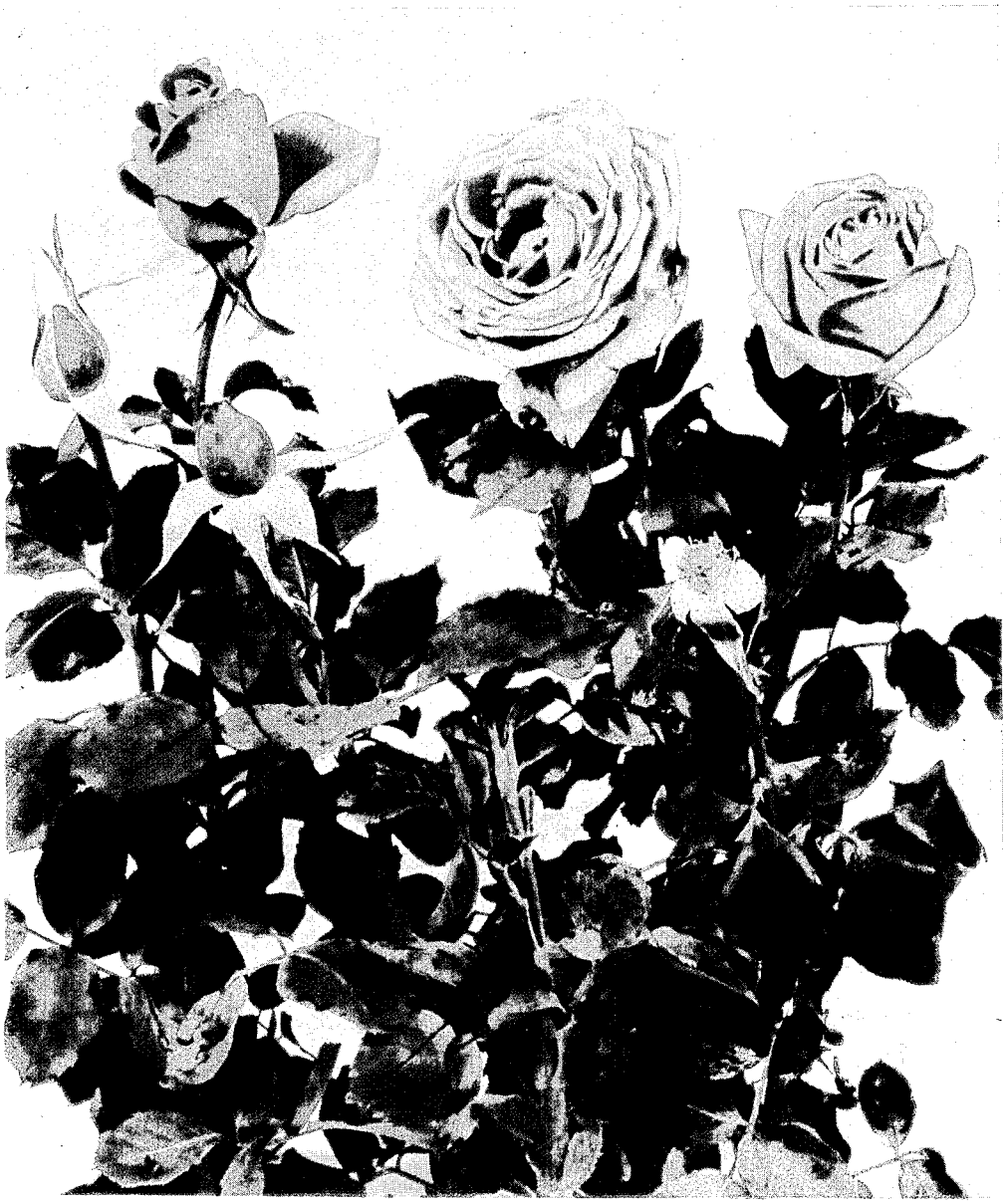
Inventor
H. C. Swim
By Robb & Robb
attorneys Patented Mar. 16, 1948

Plant Pat. 791

UNITED STATES PATENT OFFICE

791

ROSE PLANT

Herbert C. Swim, Ontario, Calif., assignor, by mesne assignments, to Mount Arbor Nurseries, Shenandoah, Iowa, a corporation of Iowa Application February 13, 1947, Serial No. 728,339

1 Claim. (Cl. 47—61)

The present invention relates to a new and distinct variety of hybrid tea rose plant, originated by crossing the variety "Charlotte Armstrong" (Pl. Pat. #455) with the well-known variety "Night" (unpatented).

The former of these parents produces blooms of rich cerise color, while those of the pollen parent are deep crimson shaded black to maroon.

This new variety is entirely distinguishable from either of its parents not only as to the coloring of flowers, but is also dominantly distinct and novel from other hybrid tea rose plant varieties in relation to the following characteristics:

(1) An upright-growing plant with greater vigor and floriferousness than other very double roses in its color class substantially as disclosed herein.

(2) Greater length and distinctive form of the bud as compared with other varieties in the petalage and color class of this new variety.

(3) Whereas in most varieties of roses more and larger prickles are found on the main stems than on the branches, this new variety has very few large prickles and relatively few small prickles on the main stems but relatively many small prickles on the branches. This freedom from large prickles on the main stems permits the plants to be more easily handled by both producer and consumer.

(4) Abundant, large, flat, leathery leaves covering the plant well and adding to its attractiveness.

(5) The leaves are above average for roses of this color range in their resistance to mildew.

A sexual reproduction of this new variety shows the foregoing characteristics come true to form and are established.

The accompanying drawings illustrate specimens of this new variety, showing the flowers in different stages of development from bud to full-open bloom and the prolific nature of the foliage background for these blooms.

The following is a detailed description of the new variety, color terminology being in accordance with Robert F. Wilson's Horticultural Colour Chart with exceptions noted from Ridgway's Color Standards and Nomenclature:

Type: Hardiness untested; bush; outdoor; seedling; for cut flowers and garden decoration.

Class: Hybrid tea.

Breeding: Seedling.

*Seed parent.*—"Charlotte Armstrong."

*Pollen parent.*—"Night."

Propagation: Holds its distinguishing characteristics through succeeding propagations by budding.

*Flower*

Locality where grown: Ontario, California.

Flowers borne: Singly, sometimes two to three, to stem; on normal, medium length stems.

Quantity of bloom: Free; outdoors.

Continuity: Continuous during growing season.

Fragrance: Penetrating; spicy.

Bud:

*Peduncle.*—Medium length; medium to heavy; erect; medium rough; numerous gland-tipped cilia and prickles. *Color*—near Light Cress Green, Plate XXXI (Ridgway), becoming overlaid on sunny side or late in season with Claret Brown, Plate I (Ridgway).

*Before calyx breaks.*—*Size*—medium. *Form*—ovoid to pointed; medium length; with gland-tipped cilia on the surface of the bud; with slender, much cut foliaceous parts extending beyond the tip of the bud equal to ¾ or more of its length.

*As calyx breaks.*—*Color*—Cardinal Red, Plate 822, page 168, with shadings of Chrysanthemum Crimson, Plate 824/1, page 169. *Inner surface*—with fine tomentum. When the margin of a sepal is not covered by the margin of an adjacent sepal, it has tomentum and stipitate glands on both margins, but if margin is covered by adjacent sepal margin, it has only woolly tomentum on the margin.

*As first petal opens.*—*Size*—medium to large. *Form*—short to medium; ovoid. *Color*—outside: Cardinal Red, Plate 822/3, page 168, shading to Cardinal Red, Plate 822/1, page 168, at margin of petal. Inside: center of petal near Blood Red, Plate 820, page 166, shading to Currant Red, Plate 821/1, page 167, at margin of petal with a blotch of Lemon Yellow, Plate 4, page 4, at base of petal.

*Opening.*—Opens up well.

Bloom: Size, when fully open—medium; 3½ inches to 4½ inches.

*Petalage.*—From 55 to 65 petals plus 5 to 7 petaloids, arranged irregularly.

*Form.*—High center, at first; becoming open; petals remaining at first loosely rolled outward at tips; becoming later, at maturity, tightly rolled outward at tips.

Petals: Leathery; with inside velvety and outside satiny.

*Shape.*—Outside—broadly obovate with apex rounded. Intermediate—obovate with apex obtuse. Inside—obovate cuneate, apex obtuse.

*Color.*—Colors may be modified by being blotched, shaded, with other colors or faded.

This description of a newly opened flower was made from a rose grown outdoors in the month of October at Ontario, California:

*Color.*—*Outside petal*—outside surface: Center of petal Rose Red, Plate 724/1, page 158, shading to Currant Red, Plate 821/3, page 167, at margin of petal, blotched with Indian Yellow, Plate 6/1, page 6, at base of petal; inside surface: Center of petal Rose Red, Plate 724/1, page 158, shading to Currant Red, Plate 821/3, page 167, at margin of petal, blotched with Indian Yellow, Plate 6/1, page 6, at base of petal. *Intermediate petal*—outside surface: Cardinal Red, Plate 822/2, page 168, with small blotch of Indian Yellow, Plate 6, page 6, at base of petal; inside surface: Blood Red, Plate 820, page 166, with shadings of Currant Red, Plate 821/2, page 167, with a blotch of Indian Yellow, Plate 6, page 6, at base of petal. *Inner petal*—outside surface: Cardinal Red, Plate 822/2, page 168, with small blotch of Indian Yellow, Plate 6, page 6, at base of petal; inside surface: Blood Red, Plate 820, page 166, with shadings of Currant Red, Plate 821/2, page 167, with a blotch of Indian Yellow, Plate 6, page 6, at base of petal.

This description was made from a rose that was open for three days outdoors in the month of October, at Ontario, California:

*Color.*—*Outside petal*—outside surface: Rose Red, Plate 724/3, page 158, fading to Fuchsia Purple, Plate 28/1, page 28, with a small blotch of Lemon Yellow, Plate 4/2, page 4, at base of petal; inside surface: Rose Red, Plate 724/3, page 158, fading to Fuchsia Purple, Plate 28/1, page 28, blotched with Lemon Yellow, Plate 4/2, page 4, at base of petal. *Inside petal*—outside surface: Rose Red, Plate 724/2, page 158, with small blotch of Lemon Yellow, Plate 4/2, page 4, at base of petal; inside surface: Rose Red, Plate 724/1, page 158, blotched with Lemon Yellow, Plate 4/2, page 4, at base of petal.

*General color effect.*—Newly opened flower—Currant Red, Plate 821/2, page 167. Three days open—Rose Red, Plate 724/1, page 158.

*Behavior.*—Drop off cleanly; affected by hot weather, fading from Currant Red, Plate 821/2, page 167, to Rose Red, Plate 724/1, page 158.

*Flower longevity.*—On bush in garden, 3 to 4 days in October. Cut roses grown outdoors kept at living-room temperatures, 3 to 4 days in October.

*Reproductive organs*

Stamens: Few to medium; arranged irregularly about pistils, mixed with petaloids.

Filaments: Short, 3 to 7 mm. in length. *Color*—Saffron Yellow, Plate 7/2, page 7; most with anthers.

Anthers: Medium size: all open at once approximately. *Color*—edges Buttercup Yellow, Plate 5/1, page 5, center near Lemon Yellow, Plate 4/2, page 4.

Pollen: Sparse to moderate. *Color*—Yellow Ochre, Plate 07, page 101.

Pistils: Medium number; approximately 55 in number.

Styles: Uneven; short to medium; medium heavy; loosely bunched. *Color*—base near Uranium Green, Plate 63/3, page 63, gradually becoming Cherry, Plate 722/1, page 157, at stigma.

Stigma: Pinkish-White, somewhat translucent.

Hips: This variety very seldom sets seed under normal growing conditions.

Sepals: Usually moderately short; more or less straight; spear-shaped.

*Plant*

Foliage:

*Leaves.*—Compound of five to seven leaflets; abundant; large; heavy; leathery; dull.

*Leaflets.*—Shape—oval, with apex acute; base round; margin serrate.

*Color.*—*Mature*—upper surface: between Kronbergs' Green, Plate XXXI (Ridgway) and Yew Green Plate XXXI (Ridgway); under surface: between Light Grape Green, Plate XLI (Ridgway) and Asphodel Green, Plate XLI (Ridgway). *Young*—upper surface: Light Hellebore Green, Plate XVII (Ridgway) washed with Dark Indian Red, Plate XXVII (Ridgway); under surface: Asphodel Green, Plate XLI (Ridgway) washed with Hydrangea Red, Plate XXVII (Ridgway).

*Rachis.*—Medium heavy. Upper side: Grooved; stipitate glands on edges; under side: Moderately smooth; few prickles and stipitate glands.

*Stipules.*—Moderately long; medium wide; with moderately long points, turning out at an angle of more than 45°, slightly recurved toward the stem.

*Disease.*—Somewhat resistant to mildew.

Growth:

*Habit.*—Upright; much branched.

*Growth.*—Free.

*Canes.*—Medium to heavy.

*Main stems.*—Color—near Rainette Green, Plate XXXI (Ridgway) becoming overlaid with Warm Sepia, Plate XXIX (Ridgway) on sunny side or late in season.

*Large prickles.*—Very few; medium length; slightly hooked downward; with medium narrow base. Color—between Walnut Brown, Plate XXVIII (Ridgway) and Vandyke Brown, Plate XXVIII (Ridgway).

*Small prickles.*—Few. Color—between Walnut Brown, Plate XXVIII (Ridgway) and Vandyke Brown, Plate XXVIII (Ridgway).

*Hairs.*—None.

*Branches.*—Color—light Cress Green, Plate XXXI (Ridgway) becoming overlaid with Warm Sepia, Plate XXIX (Ridgway) on sunny side or late in season. *Large prickles*—short to medium; slightly hooked downward; with medium narrow base. Color—near Snuff Brown, Plate XXIX (Ridgway). *Small prickles*—several to many. Color—near Snuff Brown, Plate XXIX (Ridgway). *Hairs*—none, but with stipitate glands.

*New shoots.*—Color—near Light Cress Green, Plate XXXI (Ridgway) slightly washed with Hydrangea Red, Plate XXVII (Ridgway). *Large prickles*—few; medium length; slightly hooked downward with medium narrow base. Color—near Hydrangea Red, Plate XXVII (Ridgway). *Small prickles*—several to many. Color—near Hydrangea Red, Plate XXVII (Ridgway). *Hairs*—none, but with stipitate glands.

To summarize the distinctions of this new variety from each of its parents, it is noted that it is distinct from "Charlotte Armstrong" because of its more upright habit of growth, the more abundant foliage of a darker green color, the leaflets of which are broader in relation to width than those of "Charlotte Armstrong"; flowers with a deeper shade of red with more petals of a smaller size, particularly in the center of the flower, with an entirely different arrangement of these petals. It differs also in having fewer thorns of both large and small size on the large canes particularly. The form of the buds in this new variety is more ovoid than long-pointed as are the buds of "Charlotte Armstrong," and both buds and open blooms of this new variety have an intense, spicy fragrance as contrasted with the mild fragrance of the flowers of this parent.

This new variety is distinct from its pollen parent, "Night," because of its greater vigor of growth, more abundant and more mildew resistant foliage, a lighter and more glowing shade of red in the flowers which have several times as many petals as those of the pollen parent variety. The flowers of this new variety also have a more lasting substance and heavier texture than those of "Night." In addition, this new variety is very much more resistant to rose rust than its pollen parent "Night" which is well-known for its susceptibility to this disease.

I claim:

A new and distinct variety of Hybrid Tea rose plant, characterized as to novelty by the color of the flowers; by the greater length and the form, of the bud as compared with other varieties in the same petalage and color class; by the upright-growing habit of the plant, of greater vigor and floriferousness than found in other very double roses in the same color class; by the abundance of large, flat, leathery leaves; the above-average resistance of the leaves to mildew for roses of the color range of this variety; and the scarcity of large and small prickles on the main stems but relatively greater number of small prickles on the branches, substantially as shown and described.

HERBERT C. SWIM.